United States Patent
Gröger et al.

(10) Patent No.: US 7,632,665 B2
(45) Date of Patent: Dec. 15, 2009

(54) COUPLED COFACTOR-DEPENDENT ENZYMATIC REACTION SYSTEMS IN AQUEOUS MEDIA

(75) Inventors: Harald Gröger, Hanau (DE); Claudia Rollmann, Alzenau (DE); Hendrik Hüsken, Haltern am See (DE); Helge Werner, Bruchköbel (DE); Francoise Chamouleau, Hanau (DE); Chad Hagedorn, Bellbrook, OH (US); Karlheinz Drauz, Freigericht (DE); Werner Hummel, Titz (DE)

(73) Assignee: Evonik Degussa GmbH, Essen (DE)

( * ) Notice: Subject to any disclaimer, the term of this patent is extended or adjusted under 35 U.S.C. 154(b) by 138 days.

(21) Appl. No.: 10/550,556

(22) PCT Filed: Mar. 17, 2004

(86) PCT No.: PCT/EP2004/002726

§ 371 (c)(1),
(2), (4) Date: Sep. 23, 2005

(87) PCT Pub. No.: WO2004/085662

PCT Pub. Date: Oct. 7, 2004

(65) Prior Publication Data

US 2006/0216801 A1    Sep. 28, 2006

(30) Foreign Application Priority Data

Mar. 27, 2003    (DE) ............... 103 13 971

(51) Int. Cl.
C12P 7/40    (2006.01)
C12P 1/00    (2006.01)
C12P 7/00    (2006.01)
C12P 7/02    (2006.01)
A61K 38/44    (2006.01)

(52) U.S. Cl. ................ 435/136; 435/41; 435/132; 435/155; 424/94.4

(58) Field of Classification Search ............ None
See application file for complete search history.

(56) References Cited

U.S. PATENT DOCUMENTS

| | | | |
|---|---|---|---|
| 5,795,750 | A | 8/1998 | Kruse |
| 6,242,234 | B1 | 6/2001 | Kula |
| 6,987,013 | B2 | 1/2006 | Hummel |
| 2002/0064847 | A1* | 5/2002 | Yamamoto et al. .......... 435/190 |
| 2003/0054520 | A1* | 3/2003 | Bommanus et al. ......... 435/190 |

OTHER PUBLICATIONS

Chi-Huey Wong, Dale G. Drueckhammer, and Henri M. Sweers, "Enzymatic vs. fermentative synthesis: thermostable glucose dehydrogenase catalyzed regeneration of NAD(P)H for use in enzymatic synthesis", Journal of the American Chemical Society (JACS). 1985, 107(13), 4028-4031.*

CAS Registry "2,3'-Dicloroacetophenone [21886-56-6]" and "2-Chloroacetophenone [532-27-4]" , accessed Jul. 1, 2008, 3 pages.*

Gröger, H., et al "Practical Asymmetric Enzymatic Reduction through Discovery of a Dehydrogenase-Compatible Biphasic Reaction Media" Org. Lett.; 2003; 5(2), pp. 173-176 + Supporting Information (2 pages).*

Andersson, Mats, Hans Holmberg, and Patrick Adlercreutz, "Evaluation of Alcaligenes eutrophus Cells as an NADH Regenerating Catalyst in Organic-Aqueous Two-Phase System," Biotechnol. Bioeng., vol. 57, pp. 79-86, 1998.

Bommarius, Andreas S., et al., "Synthesis and Use of Enantiomerically Pure tert-Leucine," Tetrahedron Asymmetry, vol. 6, 1995, pp. 2851-2888.

De Carvalho, Carla C.C.R., and M. Manuela R. Da Fonseca, "Maintenance of cell viability in the biotransformation of (-)-carveol with whole cells of *Rhodococcus erythropolis*," J. Mol. Catalysis B: Enzymatic, No. 19-20, Dec. 2002, pp. 389-398.

Gröger, H., et al., "Practical Asymmetric Enzymatic Reduction through Discovery of a Dehydrogenase-Compatible Biphasic Reaction Media," Organic Letters, vol. 5, No. 2, Jan. 2003, pp. 173-176.

Jonsson, A., et al., "Thermodynamic and kinetic aspects on water vs. organic solvent as reaction media in the enzyme-catalysed reduction of ketones," Biochimica et Biophysica Acta, vol. 1430, No. 2, Mar. 1999, pp. 313-322.

Kato, T., et al., "An Enzymatic Cycling Method for Nicotinamide-Adenine Dinucleotide with Malic and Alcohol Dehydrogenases," Analytical Biochemistry, vol. 53, No. 1, May 1973, pp. 86-97.

(Continued)

*Primary Examiner*—Christopher R Tate
*Assistant Examiner*—Aaron J Kosar
(74) *Attorney, Agent, or Firm*—Michael A. Sanzo; Law Office of Michael A. Sanzo, LLC

(57) ABSTRACT

The present application relates to a reaction system in which chemically valuable compounds can be obtained in high enantiomer concentrations with the aid of a coupled enzymatically operating transformation process. The coupled enzymatic reaction system comprises a cofactor-dependent enzymatic transformation of an organic compound and an enzymatic regeneration of the cofactor, wherein the reaction system operates in aqueous solution with an amount of substrate above the solubility limit thereof. In the preferred embodiments, an alcohol dehydrogenase is the cofactor-dependent enzyme, and the regeneration of the cofactor (e.g. NADH or NADPH) is acheved by means of formate dehydrogenase.

12 Claims, 4 Drawing Sheets

OTHER PUBLICATIONS

Kato, Takahiko and Yoshiyuki Suzuki, "Enzymatic Determination of Galactosylceramide Galactosidase in Tissues by NAD Cycling," Analytical Biochemistry, vol. 126, No. 1, Oct. 1982, pp. 44-51.

Liese, A., "A novel reactor concept for the enzymatic reduction of poorly soluble ketones," J. Mol. Catalysis B: Enzymatic, vol. 4, No. 1/2, Jan. 1998, pp. 91-99.

Orlich, Bernhard and Reinhard Schomaecker, "Enzymatic Reduction of a Less Water-Soluble Ketone in a Reverse Micelles with NADH Regeneration," vol. 65, No. 3, Nov. 1999, pp. 357-362.

Schmid, Andreas, et al., "Preparative regio- and chemoselective functionalization of hydrocarbons catalyzed by cell free preparations of 2-hydroxybiphenyl 3-monooxygenase," J. Mol. Catalysis B: Enzymatic, vol. 11, No. 4-6, Jan. 2001, pp. 455-462.

Written Opinion of the International Searching Authority for PCT/EP2004/002726 filed Mar. 17, 2004.

International Preliminary Report on Patentability for PCT/EP2004/002726 filed Mar. 17, 2004.

* cited by examiner

COUPLED COFACTOR-DEPENDENT ENZYMATIC REACTION SYSTEMS IN AQUEOUS MEDIA

CROSS REFERENCE TO RELATED APPLICATIONS

The present application represents U.S. national stage of international application PCT/EP2004/002726, which had an international filing date of Mar. 17, 2004, and which was published in English under PCT Article 21(2) on Oct. 7, 2004. The international application claims priority to German application 103 13 971.0, filed on Mar. 27, 2003. These prior applications are hereby incorporated by reference in their entirety.

FIELD OF THE INVENTION

The present invention relates to a coupled enzymatically operating reaction system for reduction of carbonyl compounds, which is distinguished in that it is carried out in an emulsion. In particular, the invention relates to a reaction system comprising a cofactor-dependent enzymatic transformation of an organic compound, preferably the reduction of a carbonyl compound, wherein the cofactor is regenerated enzymatically in the same system.

BACKGROUND OF THE INVENTION

The production of optically active organic compounds, e.g. alcohols and amino acids, by a biocatalytic route is increasingly gaining importance. The coupled use of two dehydrogenases with cofactor regeneration has emerged as a route for the large-scale industrial synthesis of these compounds (DE19753350).

Equation 1:

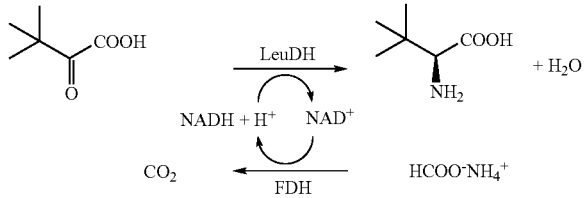

In situ regeneration of NADH with the NAD-dependent formate dehydrogenase ("FDH") in the reductive amination of trimethyl pyruvate to give L-tert-leucine (Bommarius et al. Tetrahedron Asymmetry 1995, 6, 2851-2888).

In addition to their catalytic property and efficiency, the biocatalysts efficiently employed in an aqueous medium furthermore have the advantage that in contrast to a large number of synthetic metal-containing catalysts, the use of metal-containing starting substances, in particular those which contain heavy metals and are therefore toxic, can be dispensed with. The use of expensive and furthermore hazardous reducing agents, such as, for example, borane, in the case of asymmetric reduction can also be dispensed with.

Nevertheless, difficulties occur in the reaction of substrates which are poorly water-soluble. This affects in particular the preparation of alcohols from hydrophobic carbonyl compounds, in which the substrate solubility is often below 10 mM. Similar difficulties exist in the case of poorly water-soluble products. A solution which is conceivable in principle would be to carry out the biocatalytic reduction in a polar organic solvent or a resulting homogeneous aqueous solution thereof. In this case, both the enzymes and the substrate and, where appropriate, the product should be water-soluble. A general disadvantage of a direct presence of an organic solvent, however, is the considerable reduction which generally occurs in the enzyme activity under these conditions (see e.g. Anderson et al., Biotechnol. Bioeng. 1998, 57, 79-86). In particular, FDH as the only formate dehydrogenase employed hitherto on an industrial scale and accessible in commercial amounts unfortunately has a high sensitivity towards organic solvents. This also manifests itself in the comparison examples 1 using DMSO, sulfolane, MTBE, acetone, isopropanol and ethanol as the organic solvent component in added amounts of in each case 10% (see FIG. 1).

Various set-ups are known to solve this problem relating to stabilization of the formate dehydrogenase from Candida boidinii in the presence of organic solvents, e.g. carrying out reactions by the additional use of surfactants as surface-active substances. Disadvantages here, however, are the rate of reaction, which is reduced by about a factor of 40 (!), and the inhibition of formate dehydrogenase which occurs (B. Orlich et al., Biotechnol. Bioeng. 1999, 65, 357-362). The authors furthermore note that because of the low stability of the alcohol dehydrogenase employed, a reduction process under these conditions of a microemulsion is not economical. In addition, there is a further problem in the working up, in which the resulting product must be separated from the surfactant, which has often proved to be not a trivial matter.

A possibility in principle also consists of carrying out enzymatic reactions or oxidations in a two-phase system. Here however—analogously to the abovementioned destabilizing effects in the presence of organic water-soluble solvents—only a particular class of organic solvents, namely those with a very hydrophobic character, such as, for example, heptane and hexane, has proved to be suitable. On the other hand, stability studies with other nonpolar solvents, such as toluene, but above all with typical solvents such as MTBE and ethyl acetate, showed a drastic decrease in the activity of the formate dehydrogenase from Candida boidinii even in a very short service life (H. Groger et al., Org. Lett. 2003, 5, 173-176). In the presence of heptane and hexane, in contrast, the reaction can indeed be carried out, but the solubility of the ketone substrates in these solvents is often limited.

A further possibility in principle for carrying out biocatalytic reactions consists of the use of immobilized enzymes in the organic solvent or the use of enzymes in a homogeneous solution comprising water and a water-miscible organic solvent. However, these techniques in which direct contact occurs between the organic solvent and enzyme are limited to a few enzyme classes, in particular hydrolases. It is thus noted in DE4436149 that the "direct presence of organic solvents (water-miscible or water-immiscible) is tolerated by only a few enzymes which belong to the class of hydrolases". A few further examples from other enzyme classes have indeed since become known (thus, inter alia, oxynitrilases), but the statement made in DE4436149 is still applicable to the majority of enzymes. An efficient immobilization of the FDH from Candida boidinii is thus not known. Rather, for example, it is known with the Eupergit method, as a standard tool of industrial immobilization, that the residual activity of this FDH after immobilization is <20%, which is too low for an industrial utilization. Furthermore, the immobilization itself is associated with additional costs due to the immobilization step and the immobilization materials.

Industrially, processes have therefore been developed which avoid the presence of organic solvents because of the risk of deactivation or denaturing of the enzymes. DE4436149 thus describes a process in which the product is extracted from the reaction solution into an organic solvent through a membrane, in particular a hydrophobic membrane, which is permeable to the product. Compared with a standard process in a stirred tank reactor, however, this process requires significantly more technical outlay, especially since the organic membranes required are also an additional cost factor. Furthermore, this method is suitable only for continuous processes. In addition, the disadvantage in principle of carrying out the reaction at low substrate concentrations also cannot be avoided with this method. Accordingly, the substrate concentrations are below the solubility limit, which for most ketones is 10 mM or considerably lower. However, substrate concentrations of 100 mM or above would be desirable for an industrial reaction.

Summarizing, it can be said that thus no process which helps to bypass the abovementioned disadvantages is known.

BRIEF DESCRIPTION OF THE DRAWINGS

FIG. 1 shows the results of measuring formate dehydrogenase (FDH) activity over time. Reactions are performed in water together with a variety of organic solvents. Experiments are further described in Example 1.

FIG. 2 shows the results of measuring FDH activity over time in reactions that are performed in water in the absence of organic solvent. Experiments are further described in Example 2.

FIG. 3 shows the results obtained from the reaction of 2-chloroacetophenone (250 mM) in a coupled reaction system. Reactions are carried out in phosphate buffer in the absence of organic solvent. Experiments are further described in Example 3.

FIG. 4 shows the results obtained from the reaction of 2-chloroacetophenone (400 mM) in a coupled reaction system. Reactions are carried out in phosphate buffer in the absence of organic solvent. Experiments are further described in Example 4.

FIG. 5 shows the results obtained from the reaction of 4-chloroacetophenone (250 mM) in a coupled reaction system. Reactions are carried out in phosphate buffer in the absence of organic solvent. Experiments are further described in Example 5.

FIG. 6 shows the results obtained from the reaction of 2,3'-dichloroacetophenone (300 mM) in a coupled reaction system. Reactions are carried out in phosphate buffer in the absence of organic solvent. Experiments are further described in Example 6.

FIG. 7 shows the results obtained from the reaction or cinnamaldehyde (100 mM) in a coupled reaction system. Reactions are carried out in phosphate buffer in the absence of organic solvent. Experiments are further described in Example 7.

DESCRIPTION OF THE INVENTION

Figure 1:
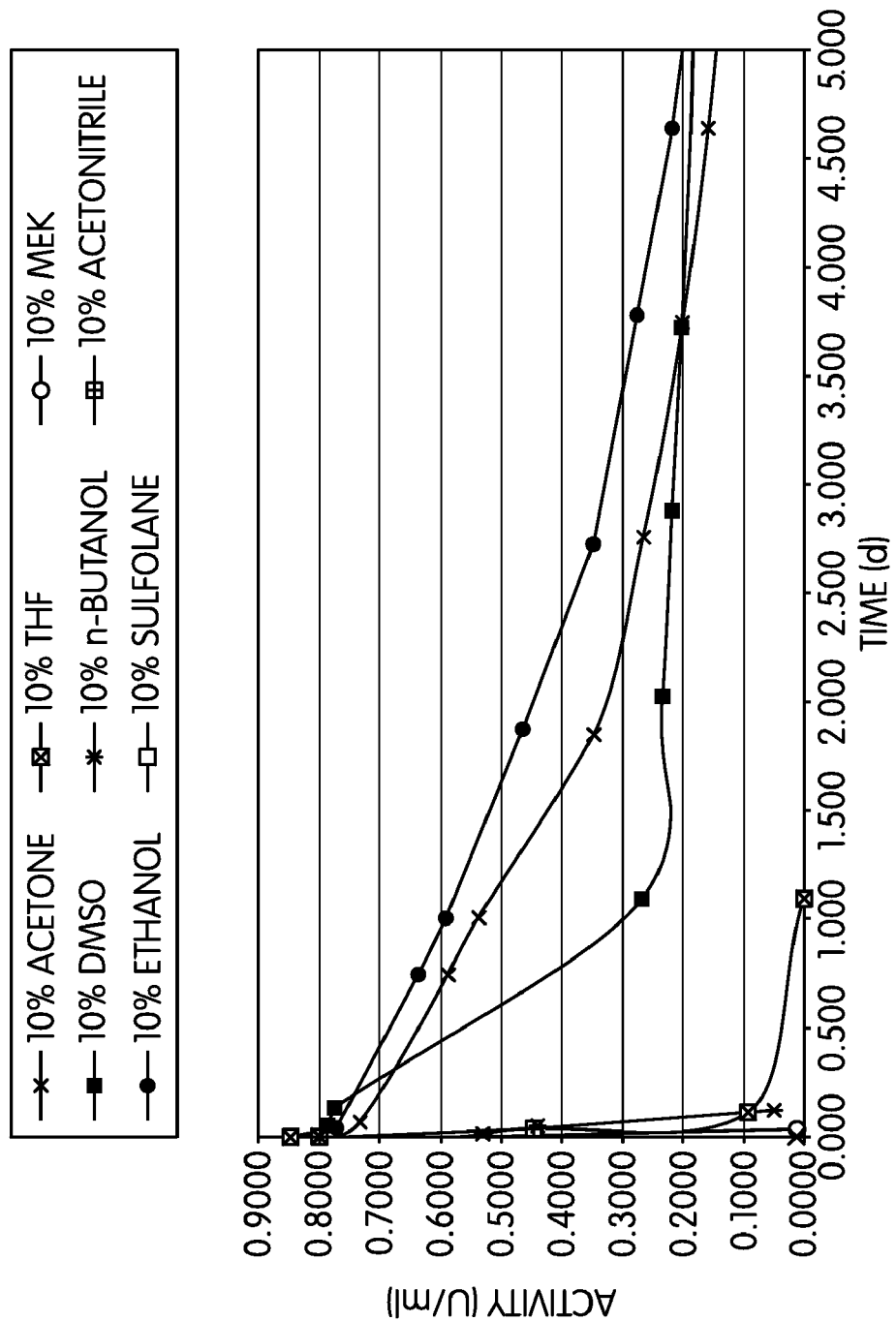
FIG. 1.

The object of the present invention was therefore to provide a possibility such that, in particular, poorly water-soluble organic compounds can be rendered accessible to a coupled cofactor-dependent enzymatic reaction to an adequate extent such that the possibility can be used on an industrial scale under, in particular, economically and ecologically advantageous conditions.

By providing a coupled enzymatic reaction system comprising a cofactor-dependent enzymatic transformation of an organic compound and an enzymatic regeneration of the cofactor in a purely aqueous solvent system without addition of surfactant, wherein the substrate is employed in the enzymatic transformation in an amount of at least 50 mM per litre of water, as long as this does not fall below the solubility limit of the substrate, the stated object is achieved in particular in a surprising, in no way foreseeable and, according to the invention, particularly advantageous manner. In contrast to the opinion which can be deduced from the prior art, in particular in view of the feared dramatic decreases in the activity of the enzymes and here in particular in that of the formate dehydrogenase from *Candida boidinii* in the presence of organic components with a logP value of <3.5 (under which also most of the substrates and products fall), it is possible, surprisingly and in spite of the direct presence of such organic components (substrates/products), to operate the coupled enzymatic reaction system without a significant loss in activity (of one) of the enzymes. Comparison example 2 underlines this surprising effect; according to this drastic decrease in activity observed in comparison example 2, with a virtually complete loss in activity of the FDH within only a few hours, it would have been expected that no significant conversions result under the reaction conditions according to the invention.

It is thus advantageous that an emulsion or a suspension is present in the reaction system at least initially. The amount of substrate employed is particularly preferably 50 to 1,500 mM, very particularly preferably 100 to 1,000 mM, and extremely preferably 100 to 500 mM per litre of water, as long as this does not fall below the solubility limit of the substrates.

The cofactor-dependent transformation is advantageously the reaction of an oxidoreductase. Carbonyl compounds, in particular aldehydes or unsymmetric ketones, can advantageously serve as the substrate for this type of conversion. These are reduced in an advantageous manner to enantiomerically enriched alcohols.

However, it is also possible to employ an alcohol compound as the substrate, in particular a primary or a chiral secondary alcohol, which is then oxidized accordingly. The nature of the reactions is diverse and includes all types of redox reactions. The present reaction system is particularly suitable for the reduction of carbonyl compounds to form enantiomerically enriched alcohols. In this context, both the reduction of aldehydes to form primary alcohols (for this see also example 7) and the asymmetric reduction of unsymmetric ketones (for this see examples 3 to 6) are of particular importance.

The reaction system can be operated with any cofactor-dependent oxidoreductase, where the cofactor is consumed by the oxidoreductase and can be regenerated by a second enzymatic system, that is to say the system is a coupled enzymatic system. Further suitable enzymes of this type can be found in the literature (Enzyme Catalysis in Organic Synthesis; Ed.: K. Drauz, H. Waldmann, Vol. I and II, VCH, 1995).

An alcohol dehydrogenase or amino acid dehydrogenase has proved to be an enzyme which it is preferable to employ.

The nature of the regeneration of the cofactor primarily depends on the cofactor employed itself. Various methods of cofactor regeneration can be found in the abovementioned literature. Under the given framework conditions of solvent, enzymes and space/time yield, the expert has a free choice of the regeneration medium. In general, in respect of NAD+ as the cofactor (in oxidation reactions) an NADH oxidase from e.g. *Lactobacillus brevis* or *L. kefir* is suitable (DE10140088). In the case of reduction reactions, regeneration of the cofactor NADH by a formate dehydrogenase has furthermore also proved to be very successful. The use of the formate dehydrogenase from *Candida boidinii* is particularly advantageous in this connection.

The cofactors which are the most usual and operate most economically under the reaction conditions are preferably used as cofactors. These are, in particular, cofactor NADH or NADPH.

The present application also provides a process for the enzymatic transformation of an organic compound using the reaction system according to the invention. The process is preferably the preparation of an enantiomerically enriched organic compound, preferably a primary or a chiral secondary alcohol.

The process procedure can be implemented as desired by the expert, with the aid of the reaction system described and the examples described in the following. The conditions which are otherwise known for the enzymatic reaction are set accordingly under the given framework conditions.

The reaction can thus preferably be carried out at temperatures of 10 to 80° C., preferably 20 to 60° C., and very preferably 20 to 40° C. When setting the temperature, the expert will be guided by framework conditions such as e.g. speed of the reaction, yield, enzyme stability and by-product spectrum.

When the reaction is complete, the now homogeneous or heterogeneous reaction mixture can advantageously be treated in a manner in which the reaction mixture is separated into an aqueous and an organic phase, if appropriate by addition of an organic solvent, and the desired product is isolated from the organic phase.

The invention also relates to a device for the transformation of organic compounds comprising a reaction system according to the invention.

Devices which are advantageously to be employed are, for example, a stirred tank or cascades of stirred tanks.

One aspect of the invention is also the use of the reaction system according to the invention for the enzymatic transformation of organic compounds or for diagnosis or analysis. In this context, the enzymatic transformation of an organic compound is preferably carried out with the formation of enantiomerically enriched products.

According to the invention, coupled enzymatic system is understood as meaning that an enzymatic transformation of an organic compound proceeds with the consumption of a cofactor and the cofactor is regenerated in situ by a second enzymatic system. As a result, this leads to a reduction in the use of expensive cofactors, since these have to be employed only in catalytic amounts—based on the total conversion.

It is particularly surprising here that in spite of current doctrine the two enzymes employed are not impaired by the presence of the emulsion and it is thus possible to prepare the desired products in very good space/time yields.

As has been shown, for both aldehydes and ketones—in contrast to most organic solvents (see comparison examples), which lead to rapid deactivation of the FDH employed—outstanding stability properties of the enzymes, in particular the very unstable formate dehydrogenase, can also still be observed after several days even at high substrate concentrations. In addition, the rapid course of the reaction, which takes place at a rate similar to that at very low ketone concentrations in purely aqueous solution (that is to say under theoretically the most optimum conditions), is very surprising. This rapid formation rate under the process conditions was in no way at all to be expected, last but not least also in view of the considerable decreases in activity on addition of ketone substrates in small amounts of <15 mM (see comparison example 2). Rather, on the basis of these considerable losses in activity even in the presence of small amounts of ketone it would have been expected that if the substrate concentration is increased further, no or only a low conversion takes place. In contrast to this expectation, the desired reaction surprisingly not only proceeds extremely rapidly under the process conditions, but also surprisingly leads to a complete conversion.

The results with the new reaction system according to the invention are reproduced in the experimental part. The comparison examples with other organic solvents are shown in FIG. 1.

The process is carried out both with the wild-type of the formate dehydrogenase from *Candida boidinii* and with a form of this enzyme modified by genetic engineering (DE19753350). As stated, NADH is preferably employed as the cofactor. For the experimental studies, for example, an ADH from *Rhodococcus*, preferably *Rhodococcus erythropolis*, can be employed as the ADH component.

In general, the enzymes employed can be used for the reaction in a cell free native or recombinantly prepared form purified as desired. In this context, crude extracts are also preferably employed.

A main advantage of this process is the simplicity of the process. Thus, it comprises no expensive process steps, and the process can be carried out in the preferred batch reactors. Likewise, in contrast to earlier processes no special membranes which separate the aqueous medium from the organic medium are required. The surfactant additions required in some processes to date are also omitted in this process. This was not to be seen from the prior art and nevertheless makes the present process extremely advantageous.

Moreover, the further downstream processing is extremely simple. A simple extraction with a water-insoluble organic solvent leads to a simple method of isolation of the product formed. The possible quantitative conversion moreover renders possible the existence of a crude product which is already highly pure—after evaporation of the organic extraction agent in vacuo. An expensive purification of the product from a (possibly also) high-boiling substrate is accordingly dispensed with.

Enantiomerically enriched or enantiomer-enriched describes the fact that one optical antipode is present in a mixture with its other to >50%.

The structures shown relate to all the possible diastereomers and, in respect of a diastereomer, to the two possible enantiomers of the compound in question which fall under this.

The process according to the invention is illustrated by the examples described below.

EXPERIMENTAL PART

Example 1

Comparison Examples of FDH Activities 2.72 g (0.8 mol/l) sodium formate and 1.14 g (0.1 mol/l) di-potassium hydrogen phosphate trihydrate are weighed out and are dissolved in 40 ml of completely demineralized $H_2O$. The pH of the solution is adjusted to 8.2 with ammonia solution (25%) and formic acid (100%) or appropriate dilutions. The solution is then transferred to a 50 ml volumetric flask and topped up with completely demineralized $H_2O$. Separately to this, 71.7 mg (4 mmol/l) $NAD^+$ trihydrate are weighed out and dissolved in approx. 20 ml of completely demineralized $H_2O$. The pH of the solution is adjusted to 8.2 with ammonia solution (25%) and formic acid (100%) or appropriate dilutions. The solution is then transferred to a 25 ml volumetric flask and topped up with completely demineralized $H_2O$. In each case 500 µl of the substrate solution and of the NADH solution are then mixed in the 1 cm cell used for the measurement. After addition of 10 µl of the enzyme solution, a 10% solution of an organic solvent (see table) in water being employed as the solvent, the mixture is shaken briefly, the cell is placed in the photometer and recording of the data is started. The enzyme solution is added only directly before the start of the measurement. The activities of the enzymes are determined after certain intervals of time by photometric detection of the reaction of $NAD^+$ to give NADH. The photometric measurement was carried out at a temperature of 30° C. and a wavelength of 340 nm with a measurement time of 15 min. The results are shown in the following in table 1 and table 2.

TABLE 1

Enzyme activity of the FDH in U/ml as a function of the solvent and time

| Time [d] | Butanol Activity [U/ml] | MEK Activity [U/ml] | DMSO Activity [U/ml] | THF Activity [U/ml] | Sulfolane Activity [U/ml] | Acetonitrile Activity [U/ml] |
|---|---|---|---|---|---|---|
| 0.000 | 0.5262 | 0.0058 | 0.7965 | 0.8492 | 0.0028 | 0.7961 |
| 0.042 | 0.0006 | 0.0011 | 0.7880 | 0.4357 | 0.0003 | 0.4494 |
| 0.125 | | | 0.7794 | 0.0414 | | 0.0840 |
| 1.097 | | | 0.2669 | | | 0.0008 |
| 2.035 | | | 0.2331 | | | |
| 2.896 | | | 0.2201 | | | |
| 5.927 | | | 0.1763 | | | |
| 7.885 | | | 0.1404 | | | |
| 9.948 | | | 0.1205 | | | |
| 13.073 | | | 0.0915 | | | |
| 14.892 | | | 0.0717 | | | |
| 16.875 | | | 0.0540 | | | |
| 19.938 | | | 0.0355 | | | |

TABLE 2

Enzyme activity of the FDH in U/ml as a function of the solvent and time

| Time [d] | Acetone Activity [U/ml] | Ethanol Activity [U/ml] |
|---|---|---|
| 0.000 | 0.8355 | 0.8491 |
| 0.042 | 0.7402 | 0.7689 |
| 0.750 | 0.5893 | 0.6367 |
| 1.000 | 0.5426 | 0.5933 |
| 1.875 | 0.3484 | 0.4687 |
| 2.760 | 0.2691 | 0.3510 |
| 3.781 | 0.2004 | 0.2814 |
| 4.646 | 0.1614 | 0.2240 |
| 5.875 | 0.1325 | 0.1736 |
| 6.778 | 0.0987 | 0.1486 |
| 7.792 | 0.0794 | 0.1277 |
| 8.729 | 0.0610 | 0.0998 |
| 11.750 | 0.0333 | 0.0536 |
| 13.726 | | 0.0421 |

Example 2

Figure 2:
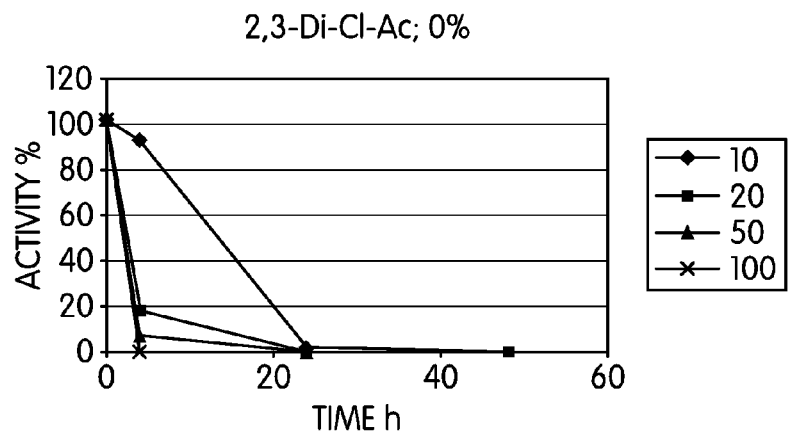
FIG. 2.

Comparison Example; Measurement of the FDH Long-Term Activities in the Presence of 2,3'-dichloroacetophenone as an Additive The activities of the formate dehydrogenase were measured in accordance with the procedure described in comparison example 1, but without the use of an organic solvent. In this context, various amounts of ketone concentration of 2,3'-dichloroacetophenone were added as an additive. The resulting course of the stability is shown in FIG. 2. When 2,3'-dichloroacetophenone was used, a rapid deactivation took place within 5 hours at substrate concentrations of >10 mM.

Example 3

Reaction with 2-chloroacetophenone at 250 mM

Figure 3:
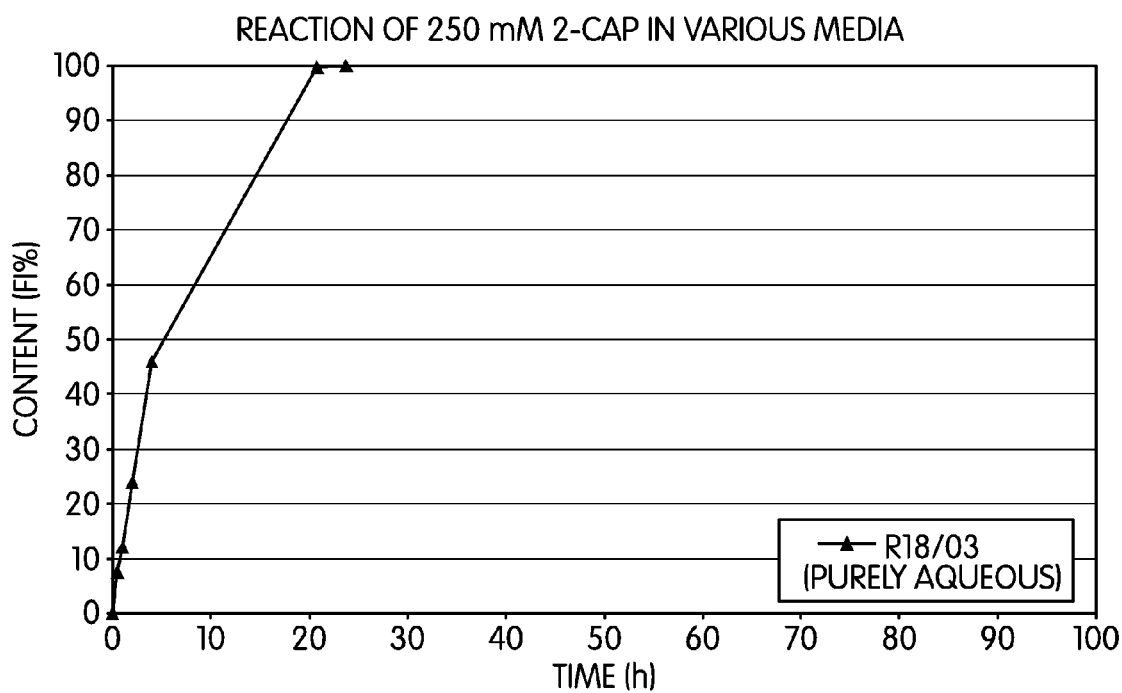
FIG. 3.

A reaction mixture, comprising ortho-chloroacetophenone (2-chloroacetophenone; 250 mM), as well as NADH (0.04 equivalent, based on the ketone), and sodium formate (5.5 equivalents, based on the ketone) at enzyme amounts of 60 U/mmol of an (S)-ADH from *R. erythropolis* (expr. in *E. coli*) and 60 U/mmol of a formate dehydrogenase from *Candida boidinii* (double mutants: C23S, C262A; expr. in *E. coli*), is stirred at a reaction temperature of 30° C. over a period of 72 hours in 50 ml of a phosphate buffer (100 mM; pH 7.0). Samples are taken during this period of time and the particular conversion is determined via HPLC. After 72 hours, complete conversion of the ketone to the desired alcohol was found. The organic components are then extracted with 2×50 ml methyl tert-butyl ether, the aqueous phase is discarded and the organic phase is dried. The filtrate which results after filtration is freed from the readily volatile constituents in vacuo and the resulting residue is investigated in respect of the formation rate by analysis via HPLC and $^1H$ nuclear magnetic resonance spectroscopy. A formation rate of >99% was determined (FIG. 3).

Example 4

Reaction with 2-chloroacetophenone at 400 mM

Figure 4:
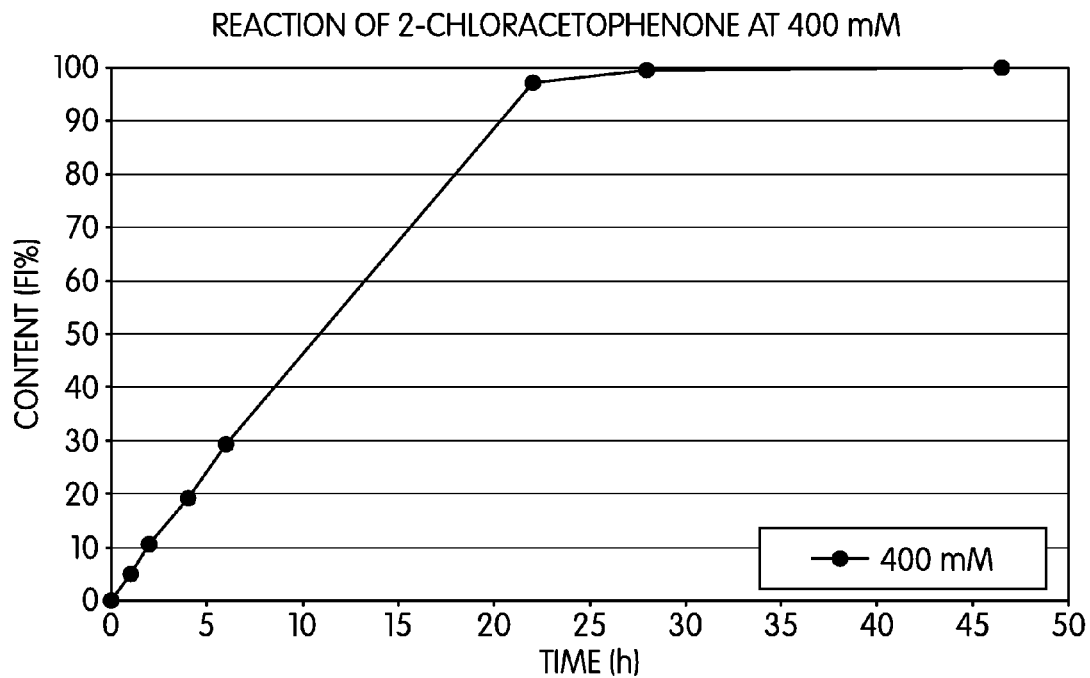
FIG. 4.

A reaction mixture, comprising ortho-chloroacetophenone (2-chloroacetophenone; 400 mM, based on the total volume), as well as NADH (0.04 equivalent, based on the ketone), and sodium formate (5.5 equivalents, based on the ketone) at enzyme amounts of 60 U/mmol of an (S)-ADH from *R. erythropolis* (expr. in *E. coli*) and 60 U/mmol of a formate dehydrogenase from *Candida boidinii* (double mutants: C23S, C262A; expr. in *E. coli*), is stirred at a reaction temperature of 30° C. over a period of 46.5 hours in 12 ml of a phosphate buffer (100 mM; pH 7.0), the total volume being 20 ml. Samples are taken during this period of time and the particular conversion is determined via HPLC. After 46.5 hours, complete conversion of the ketone to the desired alcohol was found via HPLC (FIG. 4).

Example 5

Reaction with 4-chloroacetophenone at 250 mM

A reaction mixture, comprising para-chloroacetophenone (4-chloroacetophenone; 250 mM, based on the total volume), as well as NADH (0.04 equivalent, based on the ketone), and sodium formate (5.5 equivalents, based on the ketone) at enzyme amounts of 60 U/mmol of an (S)-ADH from *R. erythropolis* (expr. in *E. coli*) and 60 U/mmol of a formate dehydrogenase from *Candida boidinii* (double mutants: C23S, C262A; expr. in *E. coli*), is stirred at a reaction temperature of 30° C. over a period of 46.5 hours in 15 ml of a phosphate buffer (100 mM; pH 7.0), the total volume being 20 ml. Samples are taken during this period of time and the particular conversion is determined via HPLC.

Figure 5:
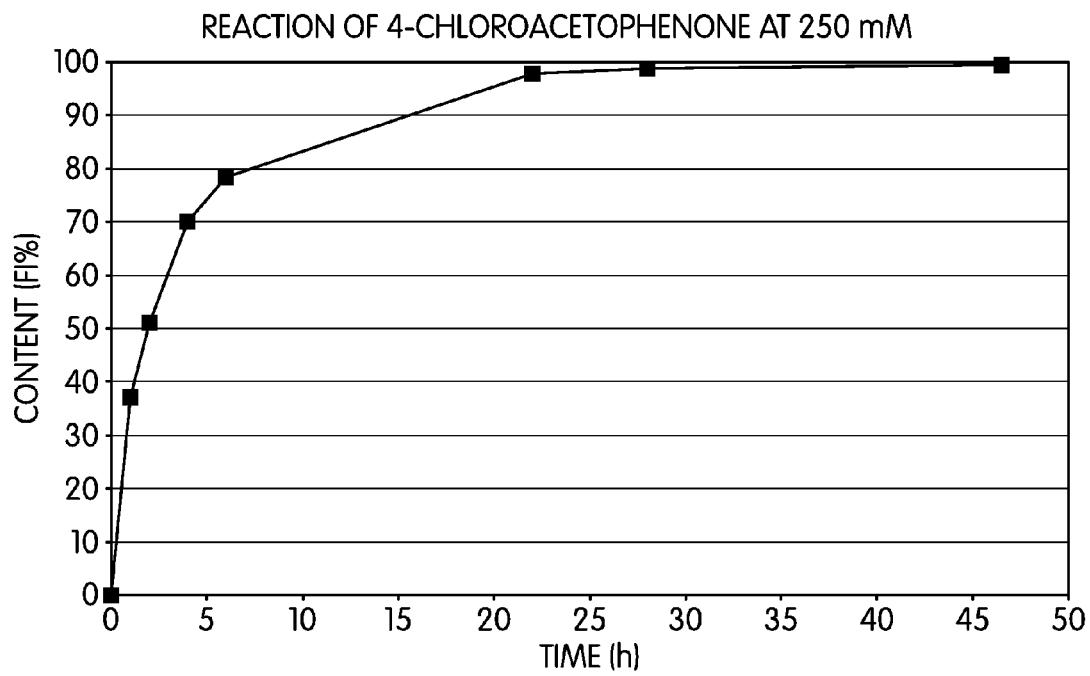
FIG. 5.

After 46.5 hours, a conversion of >99% of the ketone to the desired alcohol was found (FIG. 5).

Example 6

Reaction with 2,3'-dichloroacetophenone at 300 mM

Figure 6:
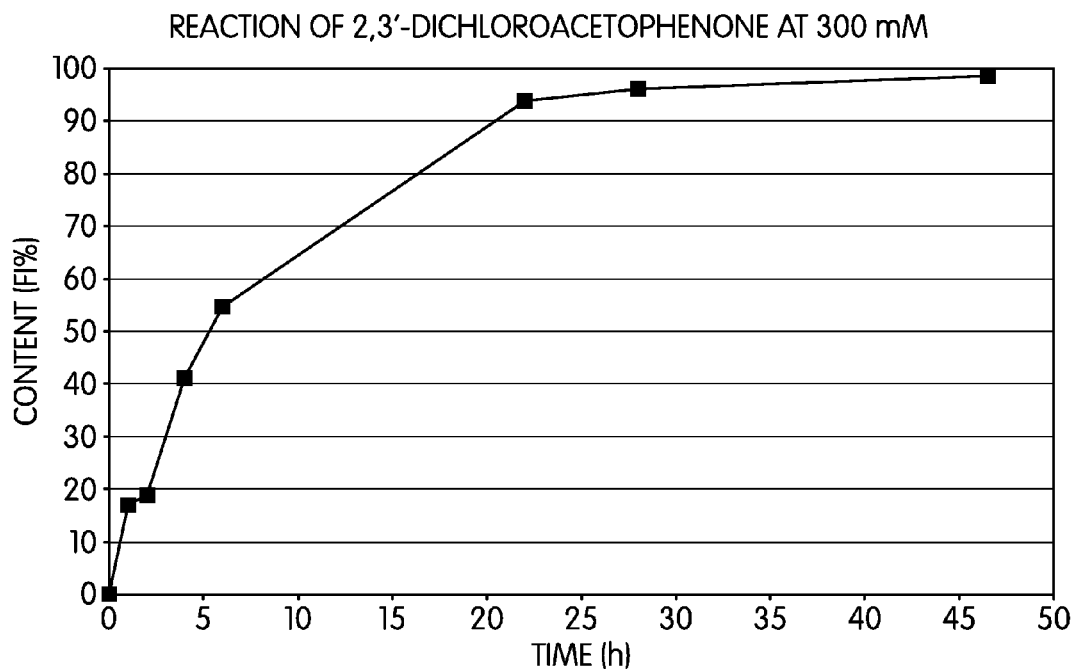
FIG. 6.

A reaction mixture, comprising alpha,meta-dichloroacetophenone 2,3'-dichloroacetonhenone; 300 mM, based on the total volume), as well as NADH (0.04 equivalent, based on the ketone), and sodium formate (5.5 equivalents, based on the ketone) at enzyme amounts of 60 U/mmol of an (S)-ADH from *R. erythropolis* (expr. in *E. coli*) and 60 U/mmol of a formate dehydrogenase from *Candida boidinii* (double mutants: C23S, C262A; expr. in *E. coli*), is stirred at a reaction temperature of 30° C. over a period of 46.5 hours in 14 ml of a phosphate buffer (100 mM; pH 7.0), the total volume being 20 ml. Samples are taken during this period of time and the particular conversion is determined via HPLC. After 46.5 hours, a conversion of >98% of the ketone to the desired alcohol was found (FIG. 6).

Example 7

Reaction with cinnamaldehyde at 100 mM

Figure 7:
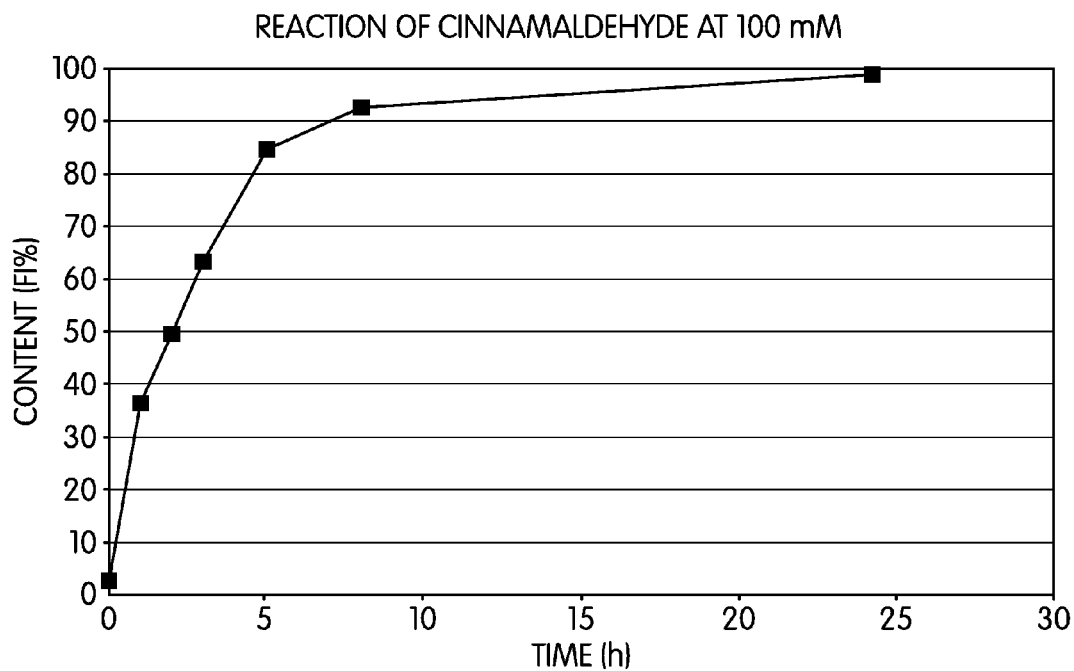
FIG. 7.

A reaction mixture, comprising cinnamaldehyde (100 mM, based on the amount of buffer employed), as well as NADH (0.2 equivalent, based on the aldehyde), and sodium formate (5.0 equivalents, based on the aldehyde) at enzyme amounts of 20 U/mmol of an (S)-ADH from *R. erythropolis* (expr. in *E. coli*) and 20 U/mmol of a formate dehydrogenase from *Candida boidinii* (double mutants: C23S, C262A; expr. in *E. coli*), is stirred at a reaction temperature of 30° C. over a period of 24.25 hours in 10 ml of a phosphate buffer (100 mM; pH 7.0). Samples are taken during this period of time and the particular conversion is determined via HPLC. After 24.25 hours, a conversion of >95% of the aldehyde to the desired alcohol was found (FIG. 7).

What is claimed is:

1. A process for producing an alcohol comprising:
   a) enzymatically reducing a carbonyl compound in a reaction mixture comprising:
      i) said carbonyl compound, wherein the carbonyl compound comprises a phenyl aldehyde or an unsymmetric phenyl ketone;
      ii) a first dehydrogenase enzyme, wherein the first dehydrogenase enzyme reduces said carbonyl compound to form said alcohol;
      iii) a substrate, wherein said substrate comprises a formate or formic acid;
      iv) a second dehydrogenase enzyme wherein said second dehydrogenase enzyme oxidizes the substrate;
      v) a cofactor for both said first dehydrogenase enzyme and said second dehydrogenase enzyme, wherein said cofactor is selected from the group consisting of NADH and NADPH; and
      vi) an aqueous solvent that does not comprise an added surfactant or an organic solvent,
   wherein the reaction mixture is in the form of an emulsion or suspension due to the concentration of said carbonyl compound being higher than or equal to its solubility limit in said aqueous solvent; and
   b) recovering said alcohol.

2. The process of claim 1, wherein said carbonyl compound is at an initial concentration in the reaction mixture of at least 50 mM.

3. The process of claim 2, wherein said carbonyl compound is at an initial concentration in the reaction mixture of between 100 and 1,000 mM.

4. The process of claim 3, wherein said process is carried out at a temperature of between 10 and 80° C.

5. The process of claim 4, wherein said recovering of said alcohol comprises adding an organic solvent to said aqueous solvent, thereby producing an organic phase, and then isolating said alcohol from the organic phase.

6. The process of claim 2, wherein said phenyl aldehyde or said unsymmetric phenyl ketone is substituted with one or more halogens.

7. The process of claim 6, wherein the initial concentration of said carbonyl compound is between 100 and 1,000 mM and said process is carried out at a temperature of between 10 and 80° C.

8. The process of claim 7, wherein said recovering of said alcohol comprises adding an organic solvent to said aqueous solvent, thereby producing an organic phase, and then isolating said alcohol from the organic phase.

9. The process of claim 2, wherein said carbonyl compound is acetophenone or acetophenone substituted with one or more halogens.

10. The process of claim 9, wherein said acetophenone substituted with one or more halogens is selected from the group consisting of 2-chloroacetophenone; 4-chloroacetophenone; and 2,3'-dichloro-acetophenone.

11. The process of claim 2, wherein said carbonyl compound is cinnamaldehyde or cinnamaldehyde substituted with one or more halogens.

12. The process of claim 4, wherein said carbonyl compound is selected from the group consisting of acetophenone, acetophenone substituted with one or more halogens, cinnamaldehyde, or cinnamaldehyde substituted with one or more halogens.

* * * * *

UNITED STATES PATENT AND TRADEMARK OFFICE
CERTIFICATE OF CORRECTION

PATENT NO. : 7,632,665 B2
APPLICATION NO. : 10/550556
DATED : December 15, 2009
INVENTOR(S) : Gröger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 210 days.

Signed and Sealed this

Second Day of November, 2010

David J. Kappos
*Director of the United States Patent and Trademark Office*